US012678421B2

(12) United States Patent
Yamamoto et al.

(10) Patent No.: US 12,678,421 B2
(45) Date of Patent: Jul. 14, 2026

(54) COMPOSITION FOR ENHANCING NAMPT GENE EXPRESSION

(71) Applicants: DAICEL CORPORATION, Osaka (JP); KYUSHU UNIVERSITY, NATIONAL UNIVERSITY CORPORATION, Fukuoka (JP)

(72) Inventors: Hiroaki Yamamoto, Tokyo (JP); Kenichi Ooe, Tokyo (JP); Yoshinori Katakura, Fukuoka (JP)

(73) Assignees: KYUSHU UNIVERSITY, NATIONAL UNIVERSITY CORPORATION, Fukuoka (JP); DAICEL CORPORATION, Osaka (JP)

( * ) Notice: Subject to any disclaimer, the term of this patent is extended or adjusted under 35 U.S.C. 154(b) by 524 days.

(21) Appl. No.: 18/024,666

(22) PCT Filed: Sep. 1, 2021

(86) PCT No.: PCT/JP2021/032115

§ 371 (c)(1),
(2) Date: Mar. 3, 2023

(87) PCT Pub. No.: WO2022/050308

PCT Pub. Date: Mar. 10, 2022

(65) Prior Publication Data

US 2023/0310367 A1 Oct. 5, 2023

(30) Foreign Application Priority Data

Sep. 4, 2020 (JP) ................................ 2020-148994

(51) Int. Cl.
*A61K 31/353* (2006.01)

(52) U.S. Cl.
CPC ................................ *A61K 31/353* (2013.01)

(58) Field of Classification Search
CPC .................................................. A61K 31/353
See application file for complete search history.

(56) References Cited

U.S. PATENT DOCUMENTS 5,952,374 A * 9/1999 Clarkson, Jr. ........ A61K 31/704
514/456
2012/0315324 A1* 12/2012 Zhang .................... A61P 35/00
514/274

FOREIGN PATENT DOCUMENTS

| | | | |
|---|---|---|---|
| CN | 103596563 | A | 2/2014 |
| JP | 2001-523258 | A | 11/2001 |
| JP | 2006-504409 | A | 2/2006 |
| JP | 2006-508942 | A | 3/2008 |
| JP | 2008-61584 | A | 3/2008 |
| JP | 2014-516359 | A | 7/2014 |
| JP | 2019-218309 | A | 12/2019 |
| WO | WO 98/50026 | A1 | 11/1998 |
| WO | WO 2003/097037 | A1 | 11/2003 |
| WO | WO 2004/009035 | * | 1/2004 |
| WO | WO 2004/009035 | A2 | 1/2004 |
| WO | WO 2004/039327 | A2 | 5/2004 |
| WO | WO 2012/107905 | A1 | 8/2012 |
| WO | WO 2012/141876 | A1 | 10/2012 |
| WO | WO 2018/079719 | A1 | 5/2018 |

OTHER PUBLICATIONS

Davinelli et al., "Enhancement of mitochondrial biogenesis with polyphenols: combined effects of resveratrol and equol in human endothelial cells," Immunity & Ageing, vol. 10, No. 28, 2013, pp. 1-5.
Guerrieri et al., "Exercise-mimetic AICAR transiently benefits brain function," Oncotarget, vol. 6, No. 21, Jul. 17, 2015, pp. 18293-18313.
Huang et al., "A critical role of nicotinamide phosphoribosyltransferase in human telomerase reverse transcriptase induction by resveratrol in aortic smooth muscle cells," Oncotarget, vol. 6, No. 13, Mar. 14, 2015, pp. 10812-10824.
International Search Report for International Application No. PCT/JP2021/032115, dated Nov. 9, 2021, with English translation.
Nichinaikaishi (The Journal of the Japanese Society of Internal Medicine), vol. 104, 2015, pp. 81-85 (6 pages total), with partial English translation.
Ota, "About the longevity gene Sirt1," Nippon Ronen Igakkai Zasshi (Japanese Journal of Geriatrics), vol. 47, No. 1, 2010, pp. 11-16 (7 pages total), with partial English translation.
Written Opinion of the International Searching Authority for International Application No. PCT/JP2021/032115, dated Nov. 9, 2021, with English translation.
Yoon et al., "SIRT1-Mediated eNAMPT Secretion from Adipose Tissue Regulates Hypothalamic NAD+ and Function in Mice," Cell Metabolism, vol. 21, May 5, 2015, pp. 706-717 (23 pages total).
Yoshino et al., "NAD+ intermediates: The biology and therapeutic potential of NMN and NR," Cell Metabolism, vol. 27, No. 3, Mar. 6, 2018, pp. 513-528.
Zhang et al., "NAD+ repletion improves mitochondrial and stem cell function and enhances life span in mice," Science, vol. 352, Issue 6292, Jun. 17, 2016, pp. 1436-1443 (9 pages total).
Chang et al., "SIRT1 Mediates Central Circadian Control in the SCN by a Mechanism that Decays with Aging," Cell, Jun. 20, 2013, pp. 1448-1460.
Man et al., "The roles of gut microbiota and circadian rhythm in the cardiovascular protective effects of polyphenols," Br. J. Pharmacol, vol. 177, 2020, pp. 1278-1293.
"Abstracts of ICI 2016," European Journal of Immunology, vol. 46, Aug. 2016, 2 pages.

(Continued)

*Primary Examiner* — Rei Tsang Shiao
(74) *Attorney, Agent, or Firm* — Birch, Stewart, Kolasch & Birch, LLP

(57) ABSTRACT

An object of the present disclosure is at least to provide a technique for enhancing expression of a NAMPT gene. The object is achieved by a composition for enhancing NAMPT gene expression, the composition containing an equol compound as an active ingredient.

15 Claims, 11 Drawing Sheets

Specification includes a Sequence Listing.

(56) References Cited

OTHER PUBLICATIONS

Park et al., "Oligonol promotes anti-aging pathways via modulation of SIRTI-AMPK-Autophagy Pathway," Nutrition Research and Practice, vol. 10, No. 1, 2016, pp. 3-10.
Satoh et al., "Effect of Soy Protein, Isoflavone Metabolite and Equol Administration on the Reduction of Cardiovascular Disease Risk in the Patients with Obesity and Metabolic Syndrome," Soy Protein Research, vol. 18, 2015, pp. 159-165, with English translation.
Tang et al., "Curcumin ameliorates chronic obstructive pulmonary disease by modulating autophagy and endoplasmic reticulum stress through regulation of Sirt I in a rat model," Journal of International Medical Research, vol. 47, No. 10, 2019, pp. 4764-4774.

* cited by examiner (mean±SEM, n=3, ***p<0.001 vs DMSO, Student' s t-test)

(mean±SEM, n=3, ***p<0.001 vs DMSO, Student's t-test)

(mean±SEM, n=3, *p<0.05 vs DMSO, Student's t-test)

(mean±SEM, n=3, ***p<0.001 vs DMSO, Student's t-test)

(mean±SEM, n=3, **p<0.01 vs DMSO, Student' s t-test)

(mean±SEM, n=3, p<0.01 *p<0.001 vs DMSO, Student' s t-test)

COMPOSITION FOR ENHANCING NAMPT GENE EXPRESSION

TECHNICAL FIELD

The present disclosure relates to a composition for enhancing NAMPT gene expression.

BACKGROUND ART

A decrease in intracellular nicotinamide adenine dinucleotide ($NAD^+$) content due to aging is known to be a cause of hypofunction of organs and tissues and causes of aging-related diseases (Non-Patent Literature 1).

Supplementation of $NAD^+$ for decreased intracellular $NAD^+$ content has been reported to improve functions of mouse mitochondria and mouse stem cells and extend the lifespan (Non-Patent Literature 2). In addition, supplementation of nicotinamide mononucleotide (NMN), which is an intermediate metabolite of $NAD^+$, has been reported to exhibit preventive and therapeutic effects on pathological conditions and disease states associated with aging (Non-Patent Literature 1).

Nicotinamide phosphoribosyltransferase (NAMPT), which is a rate-limiting enzyme in the $NAD^+$ synthesis system, is known. NMN is an enzyme reaction product of NAMPT, and $NAD^+$ synthesized from NMN activates a sirtuin (SIRT) gene, which is an $NAD^+$-dependent longevity gene.

Activation of a sirtuin gene is known to deacetylate peroxisome proliferators-activated receptor γ coactivator-1α (PGC-1α), which is a transcriptional coactivator, and enhance mitochondrial function (e.g., by increasing the number of mitochondria) (Non-Patent Literature 3).

In addition, enhanced mitochondrial function of cells constituting the intestinal tract is known to improve intestinal immunity and prevent or ameliorate viral infection (Non-Patent Literature 4). In addition, enhanced mitochondrial function of muscle cells is known to improve muscle function and improve brain function accordingly (Non-Patent Literature 5).

In addition, activation of a sirtuin gene is known to provide many benefits, such as preventing or ameliorating inflammatory bowel disease, sarcopenia, arteriosclerosis, heart disease, chronic obstructive pulmonary disease, osteoporosis, or cancer, and exerting an anti-aging effect (Patent Document 1).

Furthermore, sirtuin 1 (SIRT1), which is one of gene products of sirtuin genes, deacetylates intracellular NAMPT (iNAMPT) into extracellular NAMPT (eNAMPT), promotes eNAMPT secretion out of cells, and activates eNAMPT. eNAMPT is known to migrate into blood and promote $NAD^+$ synthesis in various organs (Non-Patent Literature 6).

Increasing NAMPT, which is a rate-limiting enzyme of the $NAD^+$ synthesis system would provide many advantages as described above. Resveratrol is known as an active ingredient for enhancing the expression of such a NAMPT gene (Non-Patent Literature 7).

On the other hand, equol, which has a female hormone-like physiological effect, is known as a component that can be utilized for prevention and amelioration of menopausal symptoms, alleviation of allergic symptoms, and the like (Patent Documents 2 and 3). However, enhancement of NAMPT gene expression by equol is not known.

CITATION LIST

Patent Document

Patent Document 1: JP 2019-218309 A
Patent Document 2: JP 2001-523258 T
Patent Document 3: Re-publication of PCT International Publication No. 03/097037

Non-Patent Literature

Non Patent Literature 1: Cell Metab., 27, 513-528 (2018)
Non-Patent Literature 2: Science, 352, 1436-1443 (2016)
Non-Patent Literature 3: Nippon Ronen Igakkai Zasshi (Japanese Journal of Geriatrics), Vol. 47, No. 1 (2010)
Non-Patent Literature 4: Nichinaikaishi (The Journal of the Japanese Society of Internal Medicine), 104: 81-85 (2015)
Non-Patent Literature 5: Oncotarget, 6; 21: 18293-18313 (2015)
Non-Patent Literature 6: Cell Metabolism, 21, 706-717 (2015)
Non-Patent Literature 7: Oncotarget, 10; 6 (13): 10812-10824 (2015)

SUMMARY OF INVENTION

Technical Problem

An object of the present disclosure is to provide a technique for enhancing expression of a NAMPT gene.

Solution to Problem

<1> A composition for enhancing NAMPT gene expression, the composition containing an equol compound as an active ingredient.

<2> The composition according to <1>, for increasing NAMPT.

<3> The composition according to <1> or <2>, for increasing $NAD^+$.

<4> The composition according to any of <1> to <3>, for activation of a sirtuin gene.

<5> The composition according to any of <1> to <4>, for deacetylation of PGC-1α.

<6> The composition according to any of <1> to <5>, for enhancing mitochondrial function.

<7> The composition according to <6>, wherein the enhancement of mitochondrial function is increasing the number of mitochondria.

<8> The composition according to any of <1> to <7>, for prevention or amelioration of inflammatory bowel disease, sarcopenia, arteriosclerosis, heart disease, chronic obstructive pulmonary disease, osteoporosis, cancer, a viral infection, or dementia.

<9> The composition according to any of <1> to <7>, for anti-aging.

<10> The composition according to any of <1> to <9>, wherein the composition is a food or beverage product.

<11> The composition according to any of <1> to <9>, wherein the composition is a pharmaceutical product.

Advantageous Effects of Invention

The present disclosure can achieve at least an effect of providing a technique for enhancing the expression of a NAMPT gene.

BRIEF DESCRIPTION OF DRAWINGS

FIG. 5-1 is photographs showing results of Example 3 according to one embodiment in the present disclosure.

FIG. 5-2 is a graph showing results of Example 3 according to one embodiment in the present disclosure.

DESCRIPTION OF EMBODIMENTS

Figure 1:
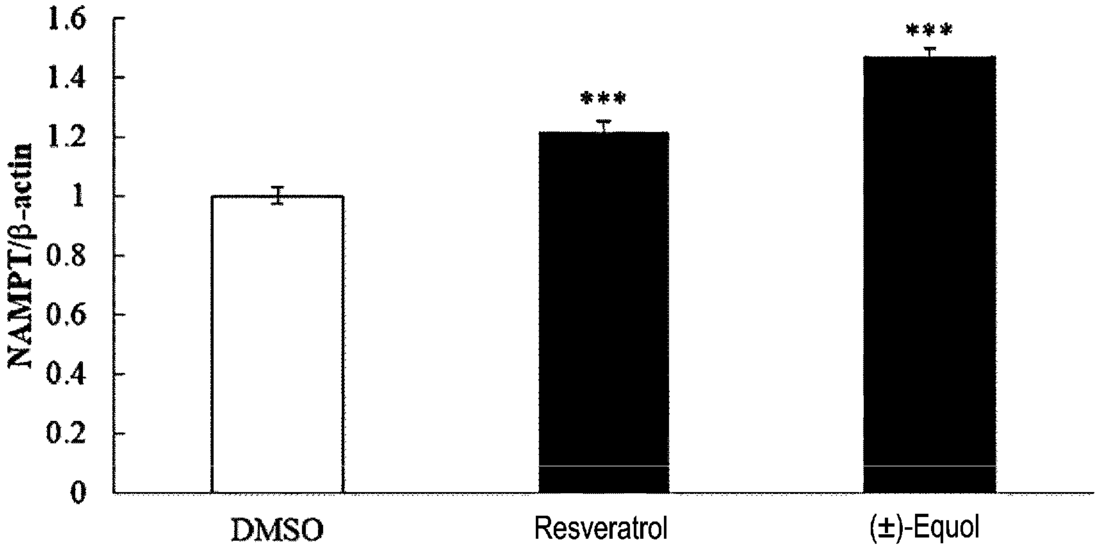
FIG. 1 is a graph showing results of Example 1 according to one embodiment in the present disclosure.

Microorganisms with an accession number beginning with the word ATCC in the present specification can be obtained from the American Type Culture Collection.

One embodiment of the present disclosure is a composition for enhancing NAMPT gene expression, the composition containing an equol compound as an active ingredient.

The equol compound is represented by General Formula (1) below:

(1)

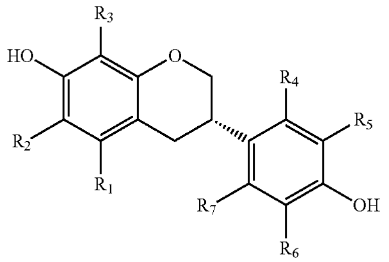

where $R_1$ to $R_7$ each represent a hydroxyl group or a hydrogen atom.

Specific examples of the equol compound include all compounds included in the compounds represented by General Formula (1) above, specifically equol (which may also be referred to as 4',7-isoflavandiol) represented by Formula (2) below and 5-hydroxy equol represented by Formula (3) below.

(2)

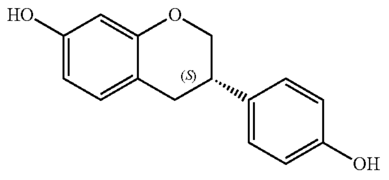

-continued (3)

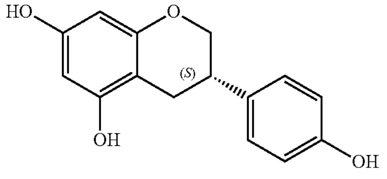

A method for obtaining the equol compound is not particularly limited; a commercially available equol compound may be used, or the equol compound may be obtained by chemical synthesis, or may be produced by a microorganism.

The composition for enhancing NAMPT gene expression according to the present embodiment (which may be referred to as the "composition according to the present embodiment" in the present specification) may contain the equol compound alone, or may contain an additional component as long as the NAMPT gene expression can be enhanced. When the composition according to the present embodiment contains the additional component, the composition according to the present embodiment may be a mixture of the equol compound and the additional component, and these components may be uniform or non-uniform.

Examples of the NAMPT gene in the present embodiment include an intracellular NAMPT (iNAMPT) gene and an extracellular NAMPT (eNAMPT) gene. The NAMPT gene in the present embodiment produces an iNAMPT protein, and the iNAMPT protein becomes an eNAMPT protein and is released out of a cell. Both proteins promote $NAD^+$ synthesis.

Examples of a subject that ingests the composition according to the present embodiment or is given the composition according to the present embodiment include mammals. Examples of the mammal include humans and non-human mammals. The non-human mammals are exemplified by cattle, goats, sheep, pigs, monkeys, dogs, cats, rats, mice, hamsters, and guinea pigs.

The content of the equol compound in terms of the total amount of the equol compound relative to the total amount of the composition according to the present embodiment is preferably 0.001 wt % or greater, more preferably 0.01 wt % or greater, and even more preferably 0.1 wt % or greater, and on the other hand preferably 20 wt % or less, more preferably 10 wt % or less, and even more preferably 5 wt % or less.

The effective intake or effective dose of the composition according to the present embodiment is appropriately set according to the subject's age, body weight, disease, disorder, symptom, and sign ("disease, disorder, symptom, and sign" may be collectively described as "disease and the like" in the present specification), the intake or administration route, the intake or administration schedule, the formulation, and the like, but is not particularly limited as long as the intake or administration of the composition to the subject enhances the expression of the NAMPT gene in the subject. The effective intake or effective dose of the composition in terms of the total amount of the equol compound is preferably 1 mg or greater, more preferably 2 mg or greater, and even more preferably 5 mg or greater per day, and on the other hand preferably 40 mg or less, more preferably 20 mg or less, and even more preferably 10 mg or less per day.

In addition, the composition according to the present embodiment may be ingested or administered once daily or may be ingested or administered multiple times per day.

Furthermore, the composition according to the present embodiment may be ingested or administered once a few days or a few weeks.

The composition according to the present embodiment contains the equol compound and enhances the expression of the NAMPT gene in a subject that has ingested the composition or has been given the composition. Thus, the composition according to the present embodiment also causes secondary and subsequent events resulting from enhanced expression of the NAMPT gene in the subject. The composition according to the present embodiment can also be used for secondary and subsequent events resulting from enhanced expression of the NAMPT gene in a subject.

Enhanced expression of the NAMPT gene increases a NAMPT protein (which may be described as "NAMPT" in the present specification). The composition according to the present embodiment can also be used for increasing NAMPT, and the present disclosure can also provide a composition for increasing NAMPT, the composition containing the equol compound as an active ingredient.

In addition, NAMPT is a rate-limiting enzyme in the $NAD^+$ synthesis system, and thus enhanced expression of the NAMPT gene increases $NAD^+$. The composition according to the present embodiment can also be used for increasing $NAD^+$, and the present disclosure can also provide a composition for increasing $NAD^+$, the composition containing the equol compound as an active ingredient.

In addition, $NAD^+$ is a substrate for a sirtuin gene, and an increase in $NAD^+$ activates a sirtuin gene, which is an $NAD^+$-dependent longevity gene. Thus, enhanced expression of the NAMPT gene activates a sirtuin gene. The composition according to the present embodiment can also be used for activation of a sirtuin gene, and the present disclosure can also provide a composition for activation of a sirtuin gene, the composition containing the equol compound as an active ingredient.

The sirtuin gene is not particularly limited as long as it is activated by an increase in $NAD^+$. Examples include sirtuin 1 gene, sirtuin 2 gene, sirtuin 3 gene, sirtuin 4 gene, sirtuin 5 gene, sirtuin 6 gene, and sirtuin 7 gene. Among them, sirtuin 1 gene deacetylates NAMPT and thus is preferred.

In addition, activation of a sirtuin gene deacetylates PGC-1α protein (which may be described as "PGC-1α" in the present specification). Thus, enhanced expression of the NAMPT gene deacetylates PGC-1α. The composition according to the present embodiment can also be used for deacetylation of PGC-1α, and the present disclosure can also provide a composition for deacetylation of PGC-1α, the composition containing the equol compound as an active ingredient.

In addition, deacetylation of PGC-1α enhances mitochondrial function. Thus, enhanced expression of the NAMPT gene enhances mitochondrial function. The composition according to the present embodiment can also be used for enhancing mitochondrial function, and the present disclosure can also provide a composition for enhancing mitochondrial function, the composition containing the equol compound as an active ingredient.

Examples of the enhancement of mitochondrial function include increasing the number of mitochondria, increasing the ability to produce ATP, and adjusting the number of cells involving apoptosis. Among them, increasing the number of mitochondria is preferred.

The composition according to the present embodiment can also be used for prevention or amelioration of a disease or the like that can be prevented or ameliorated by enhanced expression of the NAMPT gene, and the present disclosure can also provide a composition for prevention or amelioration of a disease or the like that can be prevented or ameliorated by enhanced expression of the NAMPT gene, the composition containing the equol compound as an active ingredient. "Amelioration" includes "treatment". The disease or the like can be exemplified by inflammatory bowel disease, sarcopenia, arteriosclerosis, heart disease, chronic obstructive pulmonary disease, osteoporosis, cancer, a viral infection, and dementia, as well as diseases and the like associated with any of these.

In addition, the composition according to the present embodiment can also be used for anti-aging, and the present disclosure can also provide a composition for anti-aging, the composition containing the equol compound as an active ingredient. Examples of the anti-aging include inhibition of muscle loss, inhibition of bone hypofunction and hypokinesia associated therewith, inhibition of gray hair (including hair graying), inhibition of cerebral hypofunction, inhibition of metabolic hypofunction, inhibition of hearing loss (including onset and progress of hearing loss), inhibition of diminution in visual acuity, and improvement of oral environment (e.g., inhibition of dry mouth and the like).

A preferred embodiment of the composition according to the present embodiment can be exemplified by food or beverage products (including supplements), pharmaceutical products, and feed. That is, a preferred embodiment that can be provided by the present disclosure can be exemplified by food or beverage products containing the equol compound as an active ingredient, pharmaceutical products containing the equol compound as an active ingredient, and feed containing the equol compound as an active ingredient.

The equol compound, when used as a material for food or beverage products, can be used, for example, as a food for specified health use, a nutritional supplement, a functional food, a food for sick persons, or a food additive (these include beverages) in addition to being used as a general food or beverage product. The form of the food or beverage product need not be a form of a plant or animal itself containing the equol compound. For example, the food or beverage product may be prepared by adding an appropriate auxiliary agent to the equol compound, then shaping into a form suitable for eating, such as granules, particles, tablets, capsules, or a paste, using a commonly used means, and served for eating. Alternatively, the food or beverage product may be prepared by adding the equol compound to various types of food products, for example, a processed meat food, such as ham and sausage; a processed seafood, such as kamaboko (steamed seasoned fish paste) and chikuwa (grilled tube-shaped fish paste); and bread, confectionery, butter, powdered milk, and a fermented milk product, and then used, or may be added to a beverage, such as water, fruit juice, cow's milk, or a soft drink and then used.

The food or beverage product can contain, as a main ingredient, water, a protein, a carbohydrate, a lipid, a vitamin, a mineral, an organic acid, an organic base, a fruit juice, a flavor, or the like. Examples of the protein include animal and vegetable proteins, such as whole milk powders, skimmed milk powders, partially skimmed milk powders, casein, soy proteins, chicken egg proteins, and meat proteins; their hydrolysates; and butters. Examples of the carbohydrate include sugars, processed starches (dextrin, as well as soluble starches, British starch, oxidized starches, starch esters, starch ethers, and the like), and dietary fibers. Examples of the lipid include lard; and vegetable oils and fats, such as safflower oil, corn oil, rapeseed oil, coconut oil, and their fractionated oils, hydrogenated oils, and transesterified oils. Examples of the vitamin include vitamin A, carotenes, B-group vitamins, vitamin C, D-group vitamins, vitamin E, K-group vitamins, vitamin P, vitamin Q, niacin, nicotinic acid, pantothenic acid, biotin, inositol, choline, and folic acid, and examples of the mineral include calcium, potassium, magnesium, sodium, copper, iron, manganese, zinc, selenium, and whey minerals. Examples of the organic acid include malic acid, citric acid, lactic acid, and tartaric acid. Two or more types of these components may be used in combination. Synthetic products of these components and/or food or beverage products containing these components in large amounts may be used.

The food or beverage product can be produced, for example, by a common method. In addition, the amount blended into the equol compound, the blending method, and the blending timing can be appropriately selected. Furthermore, the resulting food or beverage product can be sealed in an appropriate container, such as a bottle, a bag, a can, a box, or a pack, as necessary.

The content of the equol compound in terms of the total amount of the equol compound relative to the total amount of the food or beverage product is preferably 0.001 wt % or greater, more preferably 0.01 wt % or greater, and even more preferably 0.1 wt % or greater, and on the other hand preferably 20 wt % or less, more preferably 10 wt % or less, and even more preferably 5 wt % or less.

The effective intake of the food or beverage product is appropriately set according to the subject's age, body weight, disease or the like, its severity, the intake route, the intake schedule, the formulation, and the like, but is not particularly limited as long as the intake of the food or beverage product to the subject enhances the expression of the NAMPT gene in the subject. The effective intake of the food or beverage product in terms of the total amount of the equol compound is preferably 1 mg or greater, more preferably 2 mg or greater, and even more preferably 5 mg or greater per day, and on the other hand preferably 40 mg or less, more preferably 20 mg or less, and even more preferably 10 mg or less per day.

In addition, the food or beverage product may be ingested once daily or may be ingested multiple times per day. Furthermore, the food or beverage product may be ingested once a few days or a few weeks.

When the equol compound is used as a material for a pharmaceutical product, the method for application of the pharmaceutical product that can be employed is either oral administration or parenteral administration. When the pharmaceutical product is administered, the active ingredient is mixed with a solid or liquid non-toxic pharmaceutical carrier suitable for an administration method, such as oral administration, intrarectal administration, or injection, and then can be administered in a commonly used form of a pharmaceutical formulation. Examples of such a formulation include solid agents, such as tablets, granules, powders, and capsules; liquid agents, such as solutions, suspensions, and emulsions; and lyophilized formulations. These formulations can be prepared by common means for formulation preparation. Examples of the non-toxic pharmaceutical carrier described above include glucose, lactose, sucrose, starch, mannitol, dextrin, fatty acid glyceride, poly(ethylene glycol), hydroxyethyl starch, ethylene glycol, polyoxyethylene sorbitan fatty acid esters, amino acids, gelatin, albumin, water, and physiological saline. In addition, as necessary, a commonly used additive, such as a stabilizer, a wetting agent, an emulsifier, a binder, or an isotonizing agent, can be appropriately added.

The content of the equol compound in terms of the total amount of the equol compound relative to the total amount of the pharmaceutical product is preferably 0.001 wt % or greater, more preferably 0.01 wt % or greater, and even more preferably 0.1 wt % or greater, and on the other hand preferably 20 wt % or less, more preferably 10 wt % or less, and even more preferably 5 wt % or less.

The effective dose of the pharmaceutical product is appropriately set according to the subject's age, body weight, disease or the like, its severity, the administration route, the administration schedule, the formulation, and the like, but is not particularly limited as long as the administration of the pharmaceutical product to the subject enhances the expression of the NAMPT gene in the subject. The effective dose of the pharmaceutical product in terms of the total amount of the equol compound is preferably 1 mg or greater, more preferably 2 mg or greater, and even more preferably 5 mg or greater per day, and on the other hand preferably 40 mg or less, more preferably 20 mg or less, and even more preferably 10 mg or less per day.

In addition, the pharmaceutical product may be administered once daily or may be administered multiple times per day. Furthermore, the pharmaceutical product may be administered once a few days or a few weeks.

When the subject is a non-human mammal, the equol compound can be used as a material for feed. In this case, a feed raw material and the equol compound may be appropriately blended according to the type of mammal, the stage of growth, and the rearing environment, such as a region.

Examples of the feed raw material include grains or processed grains (such as corn, milo, and barley), bran (such as wheat bran, rice bran, and corn gluten feed); vegetable oil cakes (such as soybean oil cake, sesame oil cake, and cottonseed oil cake); animal raw materials (such as skimmed milk powder, fish meal, and meat-and-bone meal); minerals (such as calcium carbonate, calcium phosphate, sodium chloride, and silicic anhydride); vitamins; amino acids; yeasts, such as beer yeast; and fine powders of an inorganic substance (such as crystalline cellulose, talc, and silica).

The feed may be prepared by blending the feed raw material with a feed additive that is normally used in mixed feeds, such as a filler, an extender, a binder, a thickener, an emulsifier, a colorant, a flavoring, a food additive, or a seasoning, as well as an additional component (such as an antibiotic, a bactericide, an insect repellent, or a preservative) as desired.

The form of the feed is not particularly limited, and examples include powders, granules, pastes, pellets, capsules (hard capsules and soft capsules), and tablets, and the feed may be used as a pet food for pet animals or as feed for laboratory animals.

The total amount of the equol compound relative to the total amount of the feed is preferably 0.001 wt % or greater, more preferably 0.01 wt % or greater, and even more preferably 0.1 wt % or greater, and on the other hand preferably 20 wt % or less, more preferably 10 wt % or less, and even more preferably 5 wt % or less.

The effective dose of the feed is appropriately set according to the subject's age, body weight, disease or the like, its severity, the administration route, the administration schedule, the formulation, and the like, but is not particularly limited as long as the administration of the feed to a mammal enhances the expression of the NAMPT gene in the mammal. The effective dose of the feed in terms of the total amount of the equol compound is preferably 1 mg or greater, more preferably 2 mg or greater, and even more preferably 5 mg or greater per day, and on the other hand preferably 40 mg or less, more preferably 20 mg or less, and even more preferably 10 mg or less per day.

In addition, the feed may be administered once daily or may be administered multiple times per day. Furthermore, the feed may be administered once a few days or a few weeks.

EXAMPLES

Examples are described below, but none of the examples shall be construed as limiting. The following examples were all carried out at Kyushu University.

Example 1: Enhanced Expression of NAMPT, SIRT1, and PGC-1α Genes in Caco-2 Cells Human colon cancer-derived cell line Caco-2 cells (colon, epithelial-like, colorectal adenocarcinoma, human, ATCC HTB-37) were passaged using DMEM (containing 10% FBS, antibiotics (penicillin and streptomycin), and $NaHCO_3$) medium in a $CO_2$ incubator under conditions of 37° C., 5% $CO_2$, and 95% air, and used for testing.

Caco-2 cells were seeded in a 12-well plate at a cell concentration of $3\times10^5$ cells/dish, and equol dissolved in DMSO was added at a final concentration of 10 μM after 24 hours and 48 hours. In addition, the same amount of DMSO was added to a control, and resveratrol (Wako Pure Chemical Industries, Ltd.) was added to a positive control at a final concentration of 10 μM.

Cells were harvested 24 hours after the addition of equol, and total RNA was extracted. cDNA was synthesized using the total RNA and was used as a template for real-time PCR. Real-time PCR was performed using a primer of each gene and the prepared cDNA to measure the expression level of each gene. In addition, the relative gene expression level was calculated using β-actin, which is a housekeeping gene, by dividing the measured value by the expression level of β-actin. The sequences of the primers used are listed in Table 1. The orientation of the primer sequences is 5' to 3' from left to right.

TABLE 1

Primer sequences

| Primer name | Orientation | Sequence |
|---|---|---|
| β-actin-F (human) | Forward | TGGCACCCAGCACAATGAA (SEQ ID NO: 1) |
| β-actin-R (human) | Reverse | CTAAGTCATAGTCCGCCTAGAAGC (SEQ ID NO: 2) |
| NAMPT-F (human) | Forward | GGGTTACAAGTTGCTGCCACC (SEQ ID NO: 3) |
| NAMPT-R (human) | Reverse | GCAAACCTCCACCAGAACCG (SEQ ID NO: 4) |
| SIRT-1-F (human) | Forward | GCCTCACATGCAAGCTCTAGTGAC (SEQ ID NO: 5) |
| SIRT-1-R (human) | Reverse | TTCGAGGATCTGTGCCAATCATAA (SEQ ID NO: 6) |
| PGC-1α-F (human) | Forward | ACGGCATGAAGGCAATGG (SEQ ID NO: 7) |
| PGC-1α-R (human) | Reverse | CACTGGAGGCAAATTTCAGCA (SEQ ID NO: 8) |
| β-actin-F (mouse) | Forward | GGCCAGGTCATCACTATTG (SEQ ID NO: 9) |
| β-actin-R (mouse) | Reverse | GAGGTCTTTACGGATGTCAAC (SEQ ID NO: 10) |
| NAMPT-F (mouse) | Forward | CTCTTCGCAAGAGACTGCTGG (SEQ ID NO: 11) |
| NAMPT-R (mouse) | Reverse | GAGCAATTCCCGCCACAGTATC (SEQ ID NO: 12) |
| SIRT-1-F (mouse) | Forward | TCTCCTGTGGGATTCCTGAC (SEQ ID NO: 13) |
| SIRT-1-R (mouse) | Reverse | CAAACATGGCTTGAGGGTCT (SEQ ID NO: 14) |
| PGC-1α-F (mouse) | Forward | AATGCAGCGGTCTTAGCACT (SEQ ID NO: 15) |
| PGC-1α-R (mouse) | Reverse | TGTTGACAAATGCTCTTCGC (SEQ ID NO: 16) |

Figure 2:
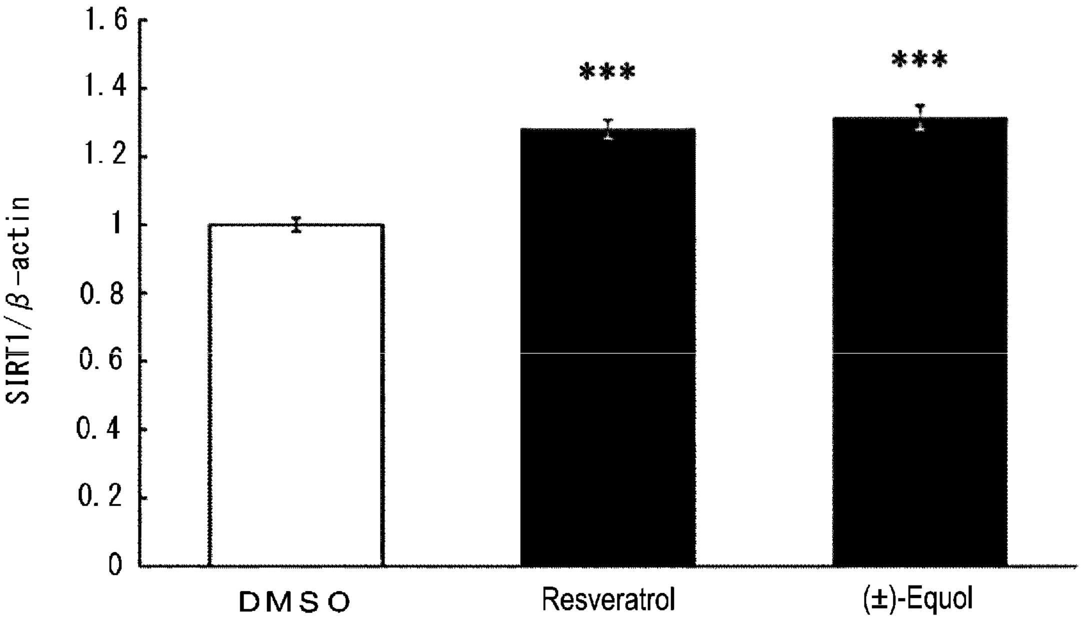
FIG. 2 is a graph showing results of Example 1 according to one embodiment in the present disclosure.
Figure 3:
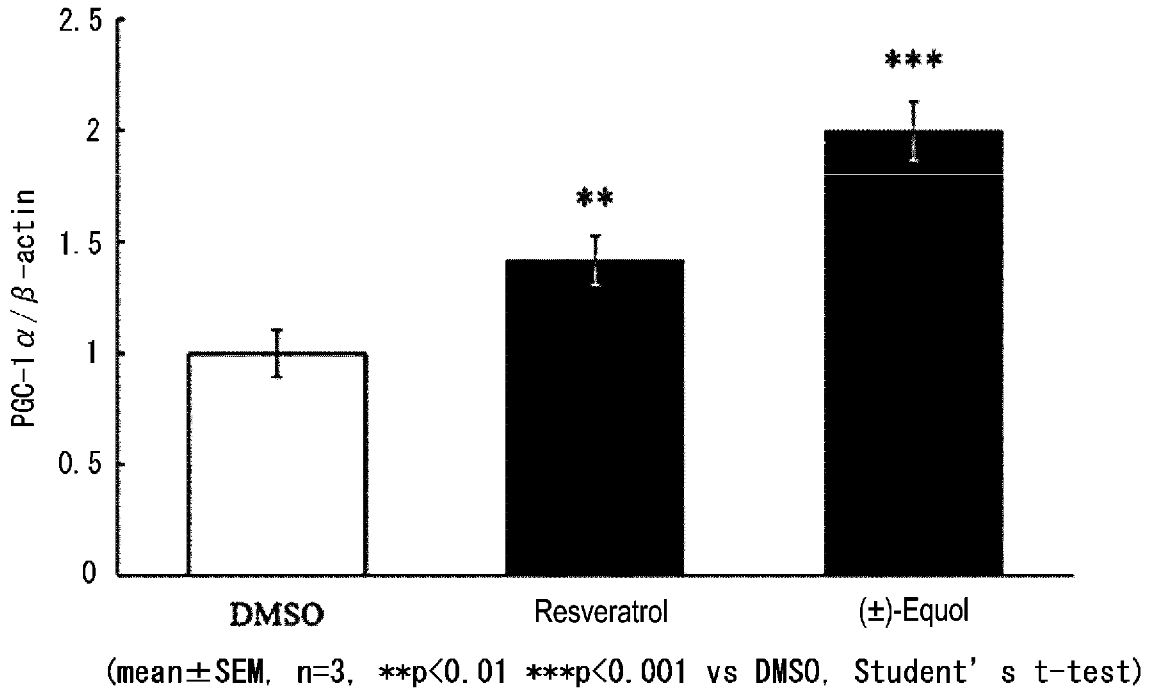
FIG. 3 is a graph showing results of Example 1 according to one embodiment in the present disclosure.

The test results are shown in FIGS. 1 to 3. As shown in FIGS. 1 to 3, equol increased the expression levels of NAMPT, SIRT1, and PGC-1α genes.

Example 2: Increased $NAD^+$ in Caco-2 Cells

Caco-2 cells were passaged in the same manner as in Example 1 and used for testing. Caco-2 cells were seeded in a 5-mL dish at a cell concentration of $3\times10^5$ cells/dish, and equol was added in the same manner as in Example 1. In addition, a control and a positive control were prepared in the same manner as well.

The medium was removed 24 hours after the addition of equol, the cells were washed with PBS, then intracellular $NAD^+$ and NADH were measured using an $NAD^+$/NADH quantification kit (BioVision, San Francisco, USA), and the $NAD^+$/NADH ratio was determined. The test results are shown in FIG. 4.

Figure 4:
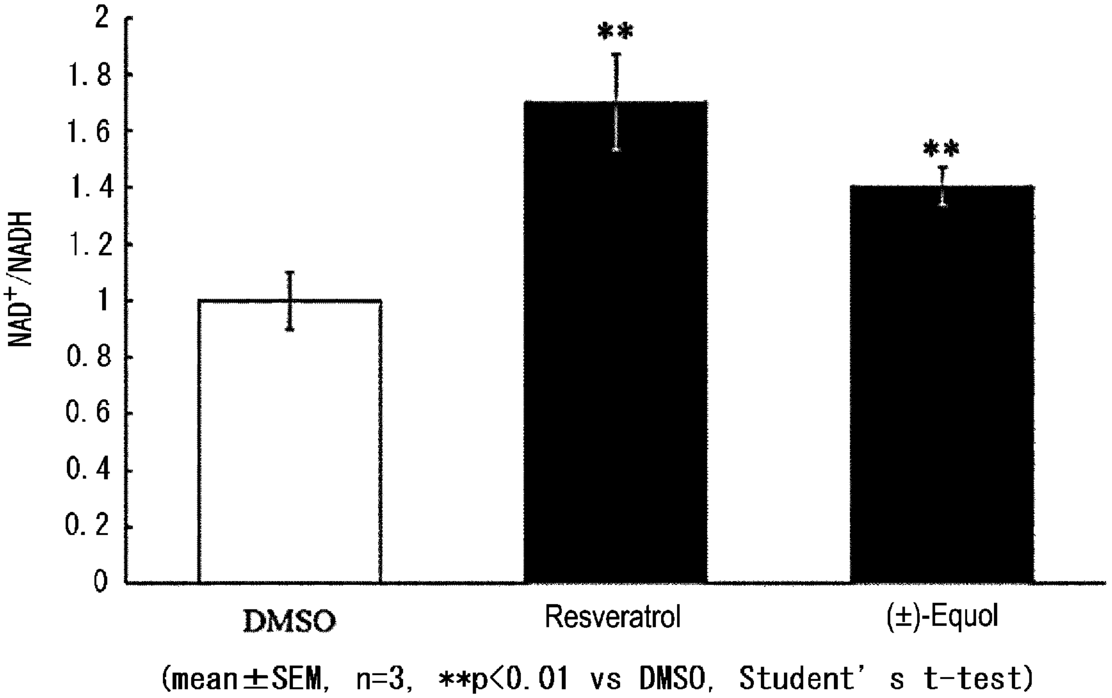
FIG. 4 is a graph showing results of Example 2 according to one embodiment in the present disclosure.

As shown in FIG. 4, equol increased $NAD^+$.

Example 3: Promotion of Deacetylation of PGC-1α in Caco-2 Cells

Caco-2 cells were passaged in the same manner as in Example 1 and used for testing. Caco-2 cells were seeded in a 5-mL dish at a cell concentration of $3\times10^5$ cells/dish, and equol was added in the same manner as in Example 1. In addition, a control and a positive control were prepared in the same manner as well.

The medium was removed 24 hours after the addition of equol, the cells were washed with PBS, and then cellular proteins were extracted. The extracted proteins were subjected to Western blotting using an anti-PGC-1α antibody (ab77210, abcam, Cambridge, UK) to measure the expression level of PGC-1α. Furthermore, after immunoprecipitation using an anti-acetylated-lysine antibody (#9441S, Cell Signaling Technology, Danvers, MA, USA), the acetyl PGC-1α level was measured by Western blotting. The test results are shown in FIGS. 5-1 and 5-2.

Figures 1, 5:
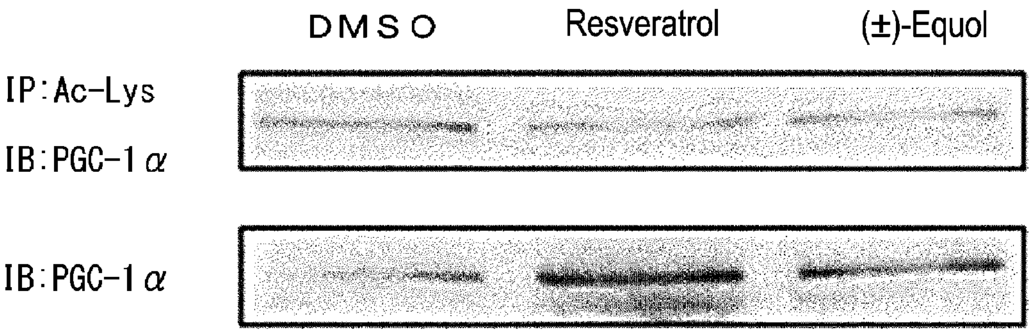
Figures 2, 5:
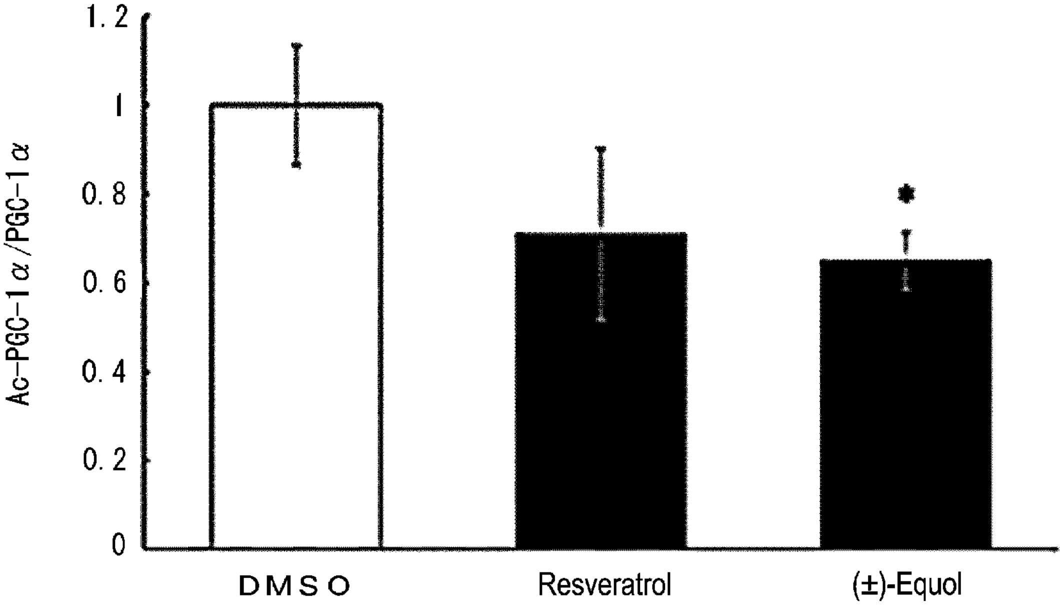

As shown in FIGS. 5-1 and 5-2, equol increased the expression level of PGC-1α and also promote deacetylation of PGC-1α.

Example 4: Promotion of Production of Intracellular Mitochondria in Caco-2 Cells Caco-2 cells were passaged in the same manner as in Example 1 and used for testing. Caco-2 cells were seeded in a μClear Fluorescence Black Plate (Greiner Bio-one) at a cell concentration of $5\times10^3$ cells/dish, and equol was added in the same manner as in Example 1. In addition, a control and a positive control were prepared in the same manner as well.

Mitochondria were stained using MotoTracker Red CMXRos (Invitrogen Corporation) 24 hours after the addition of equol. The cells were subjected to NI Cell Analyzer 1000 Imaging Cytometer (GE Healthcare Bio-Sciences Corp, Piscataway, NJ, USA) to detect intracellular mitochondria, and the image data were digitized using "mito Tracker" of NI Cell Analyzer 1000 Workstation (GE Healthcare Bio-Sciences Corp, Piscataway, NJ, USA). The test results are shown in FIG. 6.

Figure 6:
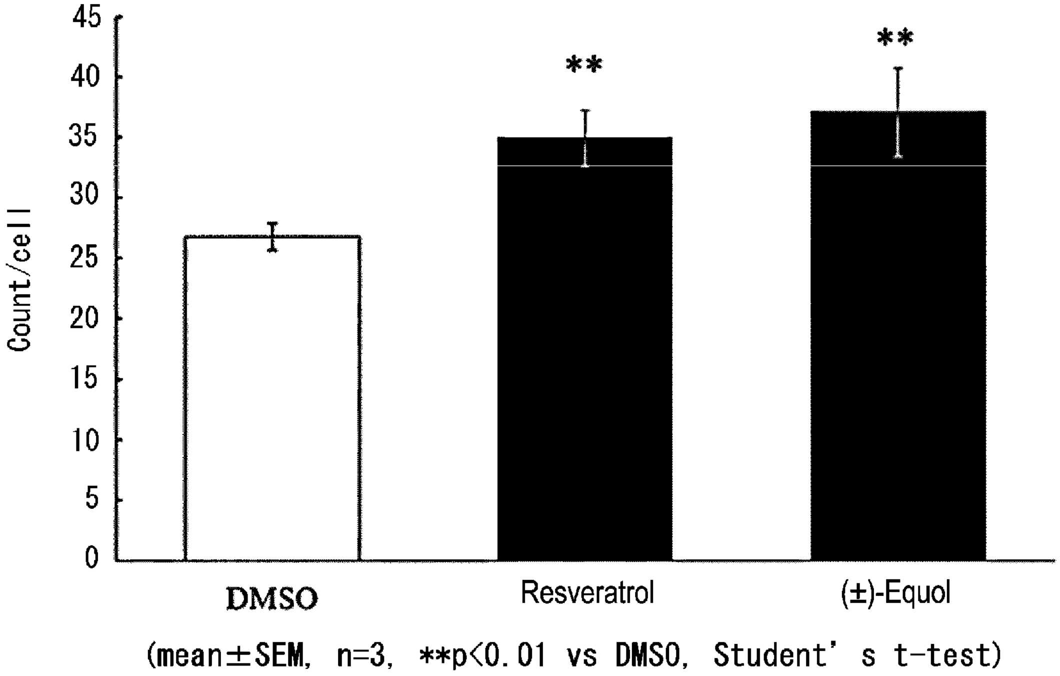
FIG. 6 is a graph showing results of Example 4 according to one embodiment in the present disclosure.

As shown in FIG. 6, equol increased the number of intracellular mitochondria.

Example 5: Increased Expression of NAMPT, SIRT1, and PGC-1α Genes in C2C12 Cells Mouse skeletal muscle-derived myoblast cell line C2C12 cells (Muscle, Myoblast, *Mus musculus*, mouse, ATCC CRL-1772 (strain C3H)) were passaged using DMEM (containing 10% FBS, antibiotics (penicillin and streptomycin), and $NaHCO_3$) medium in a $CO_2$ incubator under conditions of 37° C., 5% $CO_2$, and 95% air.

After the C2C12 cells reached about 90% confluence, the serum in the medium was replaced with inactivated horse serum, and the serum concentration was lowered to 2% to induce differentiation. Cells on day 5 after differentiation induction were used as C2C12 myotubes for testing.

C2C12 cells were seeded in a 12-well plate at a cell concentration of $3\times10^5$ cells/dish, and equol dissolved in DMSO was added at a final concentration of 10 μM after 24 hours and 48 hours. In addition, the same amount of DMSO was added to a control, and resveratrol was added to a positive control at a final concentration of 10 μM.

Cells were harvested 24 hours after the addition of equol, and total RNA was extracted. cDNA was synthesized using the total RNA and was used as a template for real-time PCR. Real-time PCR was performed using a primer of the NAMPT gene and the prepared cDNA to measure the expression level of the endogenous NAMPT gene. In addition, the relative gene expression level was calculated using β-actin, which is a housekeeping gene, by dividing the measured value by the expression level of β-actin. The sequences of the primers used are listed in Table 1.

Figure 7:
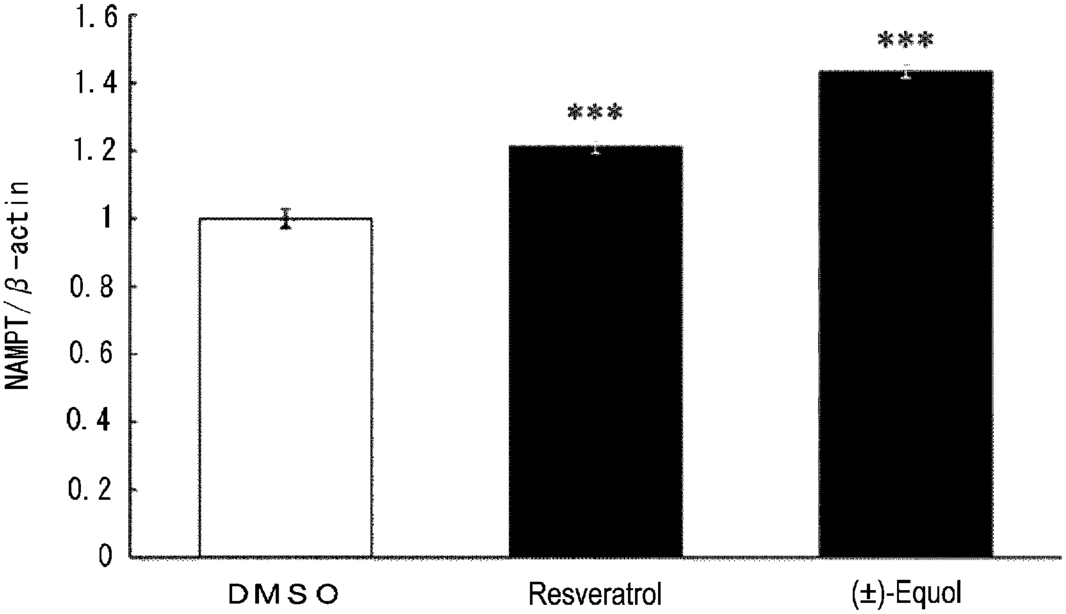
FIG. 7 is a graph showing results of Example 5 according to one embodiment in the present disclosure.
Figure 8:
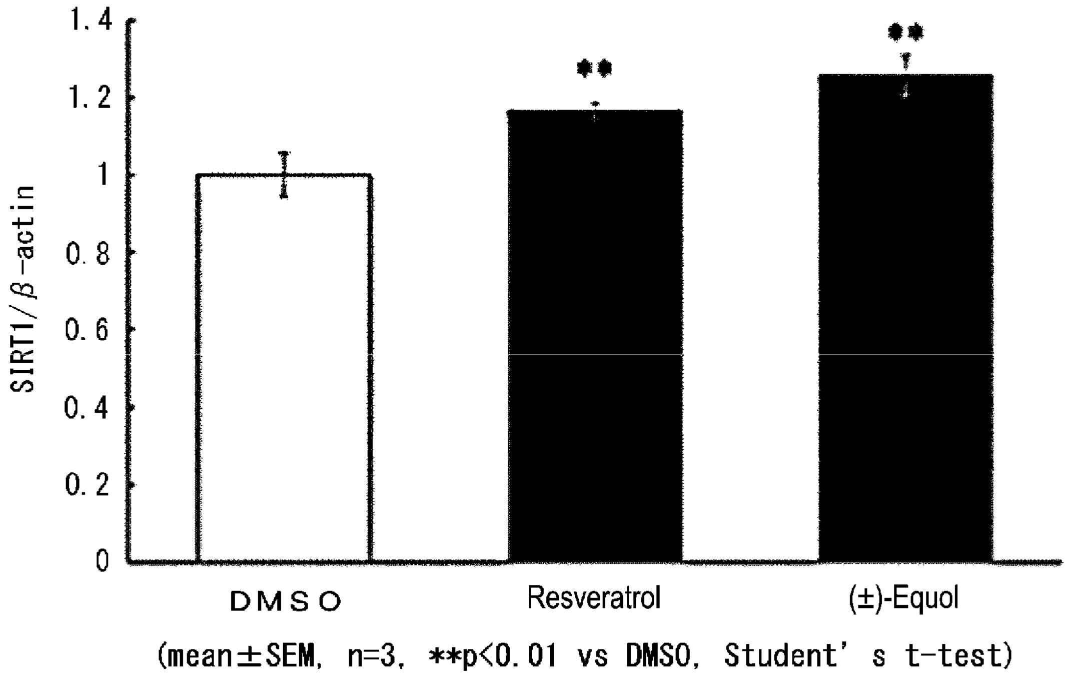
FIG. 8 is a graph showing results of Example 5 according to one embodiment in the present disclosure.
Figure 9:
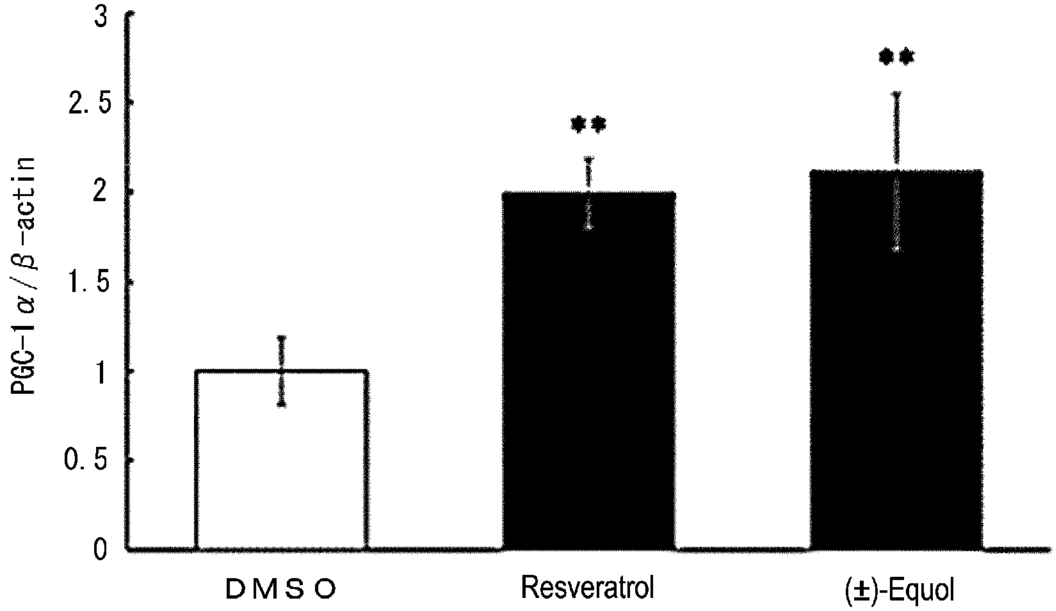
FIG. 9 is a graph showing results of Example 5 according to one embodiment in the present disclosure.

The test results are shown in FIGS. 7 to 9. As shown in FIGS. 7 to 9, equol increased the expression levels of NAMPT, SIRT1, and PGC-1α genes.

Example 6: Promotion of Production of Intracellular Mitochondria in C2C12 Cells

C2C12 cells were passaged in the same manner as in Example 7 and used for testing. C2C12 cells were seeded in a μClear Fluorescence Black Plate (Greiner Bio-one) at a cell concentration of $1\times10^4$ cells/well. After the cells reached about 90% confluence, the serum in the medium was replaced with inactivated horse serum, and the serum concentration was lowered to 2% to induce differentiation. Cells on day 5 after differentiation induction were used as C2C12 myotubes for testing.

Equol was added in the same manner as in Example 1. In addition, the same amount of DMSO was also used for a control.

The number of mitochondria was measured 72 hours after the addition of equol in the same manner as in Example 4. The test results are shown in FIG. 10.

Figure 10:
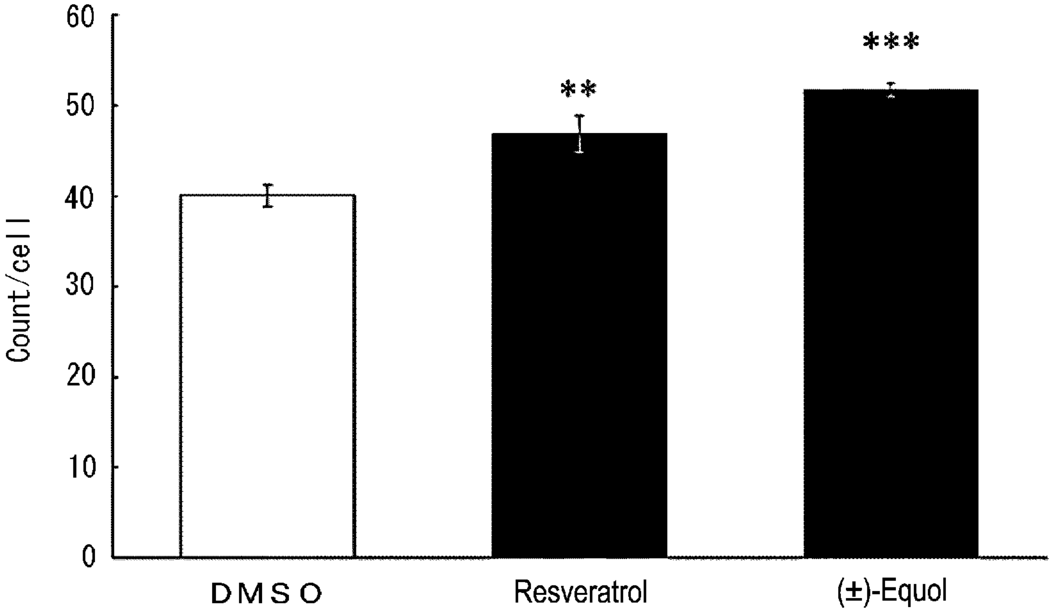
FIG. 10 is a graph showing results of Example 6 according to one embodiment in the present disclosure.

As shown in FIG. 10, equol increased the number of intracellular mitochondria.

The invention claimed is:

1. A method for enhancing NAMPT gene expression in a subject in need thereof, the method comprising administering an effective amount of an equol compound to the subject, wherein the equol compound is represented by formula (1) or a mixture of equol compounds represented by formula (1):

(1)

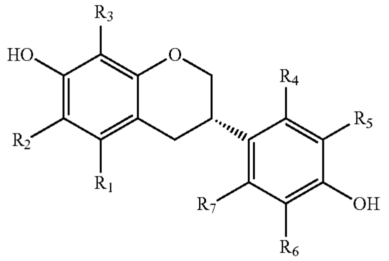

where $R_1$ to $R_7$ each represent a hydroxyl group or a hydrogen atom.

2. The method according to claim 1, wherein the equol compound is comprised in a composition.

3. The method according to claim 2, wherein the composition is a food or beverage product.

4. The method according to claim 2, wherein the composition is a pharmaceutical product.

5. A method for preventing or ameliorating sarcopenia, heart disease, chronic obstructive pulmonary disease, or a viral infection in a subject in need thereof, the method comprising administering an effective amount of an equol compound to the subject, wherein the equol compound is represented by formula (1) or a mixture of equol compounds represented by formula (1):

(1)

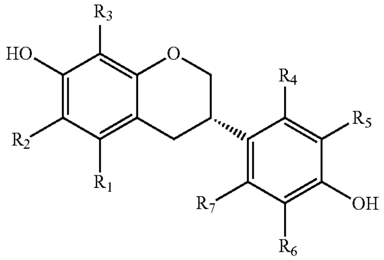

where $R_1$ to $R_7$ each represent a hydroxyl group or a hydrogen atom.

6. The method according to claim 5, wherein the equol compound is comprised in a composition.

7. The method according to claim 6, wherein the composition is a food or beverage product.

8. The method according to claim 6, wherein the composition is a pharmaceutical product.

9. A method for anti-aging in a subject in need thereof, the method comprising administering an effective amount of an equol compound to the subject, wherein the equol compound is represented by formula (1) or a mixture of equol compounds represented by formula (1):

(1)

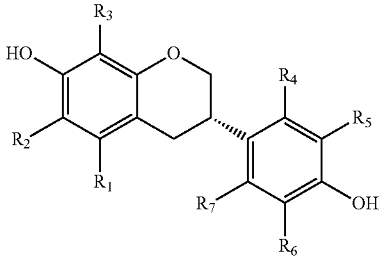

where $R_1$ to $R_7$ each represent a hydroxyl group or a hydrogen atom.

10. The method according to claim 9, wherein the equol compound is comprised in a composition.

11. The method according to claim 10, wherein the composition is a food or beverage product.

12. The method according to claim 10, wherein the composition is a pharmaceutical product.

13. The method according to claim 1, wherein the equol compound comprises at least an equol compound represented by formula (2)

(2)

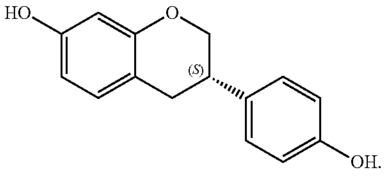

14. The method according to claim 5, wherein the equol compound comprises at least an equol compound represented by formula (2)

(2)

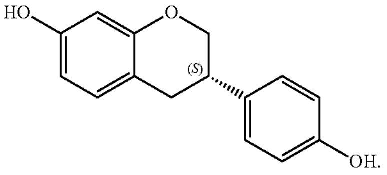

15. The method according to claim 9, wherein the equol compound comprises at least an equol compound represented by formula (2)

(2)

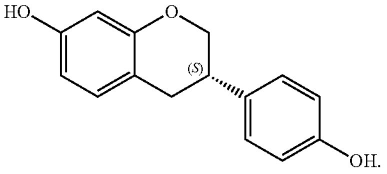

* * * * *

SEQUENCE LISTING

```
<160> NUMBER OF SEQ ID NOS: 16

<210> SEQ ID NO 1
<211> LENGTH: 19
<212> TYPE: DNA
```

-continued

<213> ORGANISM: Artificial Sequence
<220> FEATURE:
<223> OTHER INFORMATION: b-actin-F (human)

<400> SEQUENCE: 1
tggcacccag cacaatgaa 19

<210> SEQ ID NO 2
<211> LENGTH: 24
<212> TYPE: DNA
<213> ORGANISM: Artificial Sequence
<220> FEATURE:
<223> OTHER INFORMATION: b-actin-R (human)

<400> SEQUENCE: 2
ctaagtcata gtccgcctag aagc 24

<210> SEQ ID NO 3
<211> LENGTH: 21
<212> TYPE: DNA
<213> ORGANISM: Artificial Sequence
<220> FEATURE:
<223> OTHER INFORMATION: NAMPT-F (human)

<400> SEQUENCE: 3
gggttacaag ttgctgccac c 21

<210> SEQ ID NO 4
<211> LENGTH: 20
<212> TYPE: DNA
<213> ORGANISM: Artificial Sequence
<220> FEATURE:
<223> OTHER INFORMATION: NAMPT-R (human)

<400> SEQUENCE: 4
gcaaacctcc accagaaccg 20

<210> SEQ ID NO 5
<211> LENGTH: 24
<212> TYPE: DNA
<213> ORGANISM: Artificial Sequence
<220> FEATURE:
<223> OTHER INFORMATION: SIRT-1-F (human)

<400> SEQUENCE: 5
gcctcacatg caagctctag tgac 24

<210> SEQ ID NO 6
<211> LENGTH: 24
<212> TYPE: DNA
<213> ORGANISM: Artificial Sequence
<220> FEATURE:
<223> OTHER INFORMATION: SIRT-1-R (human)

<400> SEQUENCE: 6
ttcgaggatc tgtgccaatc ataa 24

<210> SEQ ID NO 7
<211> LENGTH: 18
<212> TYPE: DNA
<213> ORGANISM: Artificial Sequence
<220> FEATURE:
<223> OTHER INFORMATION: PGC-1a-F (human)

<400> SEQUENCE: 7
acggcatgaa ggcaatgg 18

-continued

<210> SEQ ID NO 8
<211> LENGTH: 21
<212> TYPE: DNA
<213> ORGANISM: Artificial Sequence
<220> FEATURE:
<223> OTHER INFORMATION: PGC-1a-R (human)

<400> SEQUENCE: 8
cactggaggc aaatttcagc a 21

<210> SEQ ID NO 9
<211> LENGTH: 19
<212> TYPE: DNA
<213> ORGANISM: Artificial Sequence
<220> FEATURE:
<223> OTHER INFORMATION: b-actin-F (mouse)

<400> SEQUENCE: 9
ggccaggtca tcactattg 19

<210> SEQ ID NO 10
<211> LENGTH: 21
<212> TYPE: DNA
<213> ORGANISM: Artificial Sequence
<220> FEATURE:
<223> OTHER INFORMATION: b-actin-R (mouse)

<400> SEQUENCE: 10
gaggtcttta cggatgtcaa c 21

<210> SEQ ID NO 11
<211> LENGTH: 21
<212> TYPE: DNA
<213> ORGANISM: Artificial Sequence
<220> FEATURE:
<223> OTHER INFORMATION: NAMPT-F (mouse)

<400> SEQUENCE: 11
ctcttcgcaa gagactgctg g 21

<210> SEQ ID NO 12
<211> LENGTH: 22
<212> TYPE: DNA
<213> ORGANISM: Artificial Sequence
<220> FEATURE:
<223> OTHER INFORMATION: NAMPT-R (mouse)

<400> SEQUENCE: 12
gagcaattcc cgccacagta tc 22

<210> SEQ ID NO 13
<211> LENGTH: 20
<212> TYPE: DNA
<213> ORGANISM: Artificial Sequence
<220> FEATURE:
<223> OTHER INFORMATION: SIRT-1-F (mouse)

<400> SEQUENCE: 13
tctcctgtgg gattcctgac 20

<210> SEQ ID NO 14
<211> LENGTH: 20
<212> TYPE: DNA
<213> ORGANISM: Artificial Sequence
<220> FEATURE:

-continued

<223> OTHER INFORMATION: SIRT-1-R (mouse)

<400> SEQUENCE: 14
caaacatggc ttgagggtct 20

<210> SEQ ID NO 15
<211> LENGTH: 20
<212> TYPE: DNA
<213> ORGANISM: Artificial Sequence
<220> FEATURE:
<223> OTHER INFORMATION: PGC-1a-F (mouse)

<400> SEQUENCE: 15
aatgcagcgg tcttagcact 20

<210> SEQ ID NO 16
<211> LENGTH: 20
<212> TYPE: DNA
<213> ORGANISM: Artificial Sequence
<220> FEATURE:
<223> OTHER INFORMATION: PGC-1a-R (mouse)

<400> SEQUENCE: 16
tgttgacaaa tgctcttcgc 20